(12) United States Patent
Glenn (10) Patent No.: US 6,712,765 B2
(45) Date of Patent: Mar. 30, 2004

(54) ULTRASONIC SCANNING METHOD AND APPARATUS

(75) Inventor: William E. Glenn, Ft. Lauderdale, FL (US)

(73) Assignee: Florida Atlantic University, Boca Raton, FL (US)

( * ) Notice: Subject to any disclaimer, the term of this patent is extended or adjusted under 35 U.S.C. 154(b) by 39 days.

(21) Appl. No.: 10/035,023

(22) Filed: Dec. 28, 2001

(65) Prior Publication Data

US 2003/0013961 A1 Jan. 16, 2003

Related U.S. Application Data

(60) Provisional application No. 60/258,833, filed on Dec. 28, 2000.

(51) Int. Cl.[7] ................................................. A61B 8/14
(52) U.S. Cl. ........................................................ 600/457
(58) Field of Search .................................. 600/437–471; 73/590–633; 310/333–335; 367/7, 11, 130, 138, 150, 103, 151

(56) References Cited

U.S. PATENT DOCUMENTS

| | | | |
|---|---|---|---|
| 4,084,582 A | | 4/1978 | Nigam ........................... 128/2 |
| 4,194,510 A | * | 3/1980 | Proudian .................... 600/445 |
| 4,325,381 A | | 4/1982 | Glenn .......................... 128/660 |

* cited by examiner

*Primary Examiner*—Ali M. Imam
(74) *Attorney, Agent, or Firm*—Martin Novack (57) ABSTRACT

An ultrasonic imaging technique and apparatus with a portable scanning head. In one form of the scanning head, a reflective scanner is provided with a variable focus, and in another form the scanning head has several reflective facts of respectively different focal lengths.

14 Claims, 5 Drawing Sheets

ULTRASONIC SCANNING METHOD AND APPARATUS

RELATED APPLICATION

The present application claims priority from U.S. Provisional Patent Application No. 60/258,833, filed Dec. 28, 2000, and said Provisional Patent Application is incorporated herein by reference.

FIELD OF THE INVENTION

This invention relates to techniques and apparatus for imaging sections of a body by transmitting ultrasonic energy into the body and determining the characteristics of the ultrasonic energy reflected therefrom and, more particularly, to an improved ultrasonic scanning technique and system for such apparatus.

BACKGROUND OF THE INVENTION

Ultrasonic imaging techniques have become common in clinical diagnosis. Ultrasonic imaging is recognized as having a number of attributes. Ultrasound differs from other forms of radiation in its interaction with living systems in that it has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparent risk associated with ionizing radiations such as X-rays.

Many diagnostic techniques using ultrasound are based on the pulse-echo method wherein pulses of ultrasonic energy are periodically generated by a suitable piezoelectric transducer. Each short pulse of ultrasonic energy is focused to a narrow beam which is transmitted into the patient's body wherein it eventually encounters interfaces between various different structures of the body. When there is a characteristic impedance mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. One common form of display is the so-called "B-scan" wherein the echo information is of a form similar to conventional television display; i.e., the received echo signals are utilized to modulate the brightness of the display at each point scanned. This type of display is found especially useful when the ultrasonic energy is scanned transverse the body so that individual "ranging" information yields individual scan lines on the display, and successive transverse positions are utilized to obtain successive scan lines on the display. The two-dimensional B-scan technique yields a cross-sectional picture in the plane of the scan, and the resultant display can be viewed directly and/or recorded. It is known that ultrasound is almost totally reflected at interfaces with gas. This has led to the use of coupling through a fluid such as water or the use of a direct-contact type of transducer. In my U.S. Pat. No. 4,084,582, there is disclosed a type of apparatus having a console which typically includes a timing signal generator, energizing and receiving circuitry, and a display/recorder for displaying and/or recording image-representative electronic signals. A portable scanning head or module, suitable for being hand held, has a fluid-tight enclosure having a scanning window formed of a flexible material. A transducer in the portable scanning module converts energy from the energizing circuitry to ultrasonic energy and also converts received ultrasound echoes back into electrical signals which are coupled to the receiver circuitry. A focusing lens is coupled to the transducer, and a fluid, such as water, fills the portable scanning module in the region between the focusing lens and the scanning window. A reflective scanning mirror is disposed in the fluid, and a driving motor, energized in synchronism with the timing signals, drives the scanning mirror in periodic fashion. The ultrasound beam is reflected off the scanning mirror and into the body being examined via a scanning window formed of a rigid material.

For a two dimensional B-scan taken with the described type of scanning head, the dimensions scanned are: (1) depth into the body, which varies during each display scanline by virtue of the ultrasound beam travelling deeper into the body as time passes; and (2) a slower transverse scan caused by the scanning mirror. The display is typically in a rectangular format, e.g. the familiar television type of display with linear sweeps in both directions. However, the transverse scan of the ultrasound beam itself, as implemented by the scanning mirror, results in a sector scan. For distances deeper in the body, the fanning out of the sectors results in geometrical distortion when displayed on a linear rectangular display. For example, the azimuth dimension in the extreme far field may be, say 2½ times larger than the azimuth dimension in the extreme near field. Thus, the density of information on the left-hand side of a conventional left-to-right display is much higher than the density of information on the right-hand side of the display. In other words, what appear to be equal distances in the body on the left and right hand sides of the display are actually substantially different distances. A solution to this problem was offered in my U.S. Pat. No. 4,325,381, wherein the scanning window was in the form of an acoustic lens for converging the scan of the ultrasound beam incident thereon from within the enclosure. The acoustic lens thereby serves to reduce geometric distortion of the scan of the ultrasound beam. In an embodiment illustrated in the referenced '381 Patent, the window/lens is formed of a rigid plastic material in a substantially plano-concave shape, with the concave surface facing the outside of the enclosure. In this embodiment, the window/lens is provided with a focal length of between one and two times the distance between the reflective scanning means and the window/lens. A focal length of about one and-a-half times the distance between the reflective scanning means and the window/lens is indicated as being particularly suitable for a functioning embodiment.

It is among of the present invention to provide improvement over prior art approaches.

It is also among the objects of the present invention to provide a technique and apparatus that will facilitate the availability of high-quality inexpensive and portable ultrasonic imaging equipment for medical applications.

SUMMARY OF THE INVENTION

By taking advantage of the computing power of a personal computer, it should be possible to make very inexpensive ultrasound scanners for medical applications. By doing this, ultrasound scanners can be used in the physician's office as well as by medical technicians operating telemedicine facilities for remote diagnosis. In order to keep the cost low, the resolution high, and the size and complexity low, it would be desirable to use a system employing mechanically scanned ultrasound because these can be made with relatively large apertures. In the previously referenced '381 Patent there is described a mechanical scanner that had a window lens or "lens membrane" at the skin surface. In the geometry described in that Patent, it was not possible to have the center of the scan to be at the focal point of the lens membrane. A form of the present invention overcomes this deficiency.

It has been found that it is generally preferable to vary the focus of the scanner rather than use dynamic focus. Variable focus maximizes the intensity and resolution at all ranges. The focus cannot be varied dynamically in transmit. In my U.S. Pat. No. 4,257,271, selectable focus was achieved using a tapped delay line and a transducer with multiple electrodes. In accordance with a further form of the invention, a variable focus technique is implemented mechanically rather than electronically. This provides a continuous variation in focus without requiring multiple electrodes on the transducer.

There are certain requirements for a scanner that has a Cartesian scan and that keeps the aperture (and consequently, the azimuth resolution) constant at all ranges. The path length from the transducer to the skin should be an integral multiple of the round trip distance the sound travels between transmit pulses. There are multiple reflections from the membrane and transducer since they are parallel to each other. This distance requirement places these multiple reflections at the membrane surfaces in the image where it cannot obscure useful information at greater depths. In previous designs, this distance was chosen to be equal to the depth of the longest range displayed by the system. Because of this, the scanning mirror had to be at a much shorter distance than this from the membrane. The focal length of the lens membrane cannot be made short enough at a reasonable scanning width to have its focal point at the center of deflection of the beam.

In a form of the present invention, a distance of twice the depth of penetration is chosen between the transducer and the membrane. The scanning mirror is placed at the depth of penetration before the membrane. The focal length of the lens membrane can now be made equal to the depth of penetration, which is also equal to the distance from the mirror to the membrane.

Embodiments of the invention are applicable to an apparatus for ultrasonically imaging sections of a body by transmitting ultrasonic energy into the body and determining the characteristics of the ultrasonic energy reflected therefrom, the apparatus including timing means for generating timing signals; energizing/receiving means operative in response to timing signals; and display/record means synchronized with the timing signals for displaying and/or recording image-representative signals from the energizing/receiving means; the apparatus having a scanning module that includes: a fluid-containing enclosure having an ultrasonically-transmissive window which can be placed in contact with the body; transducer means in the enclosure, coupled to the energizing/receiving means, for converting electrical energy to a beam of ultrasonic energy and for converting reflected ultrasonic energy to electrical signals; means for focusing the ultrasound beam emanating from the transducer means; reflective scanning means rotatably mounted in the enclosure in the path of the ultrasound beam for effecting scanning of the beam across the body via the window; the window comprising an acoustic lens for converging the scan of the ultrasound beam incident thereon from within the enclosure.

One form of the method of the invention includes the following steps: selecting a desired maximum depth of penetration of the ultrasound beam into the body; and providing distances between the transducer means and the reflective scanning means and between the reflective scanning means and the acoustic lens window that are each substantially equal to the selected maximum depth of penetration.

A further form of the method of the invention includes the following steps: providing the reflective scanning means with a controllable variable focus; and controlling the reflective scanning means to select the focusing of said reflective scanning means. In an embodiment of this form of the invention, the step of providing a reflective scanning means with a controllable variable focus comprises varying the shape of the reflective scanning means.

Another form of the method of the invention includes the following steps: providing a controllable variable focusing means in the enclosure in the path of said ultrasound beam; and controlling the variable focusing means to select the focusing thereof.

A still further form of the invention includes the following steps: providing, on the rotatable reflective scanning means, a plurality of ultrasound reflecting facets having different focusing characteristics; and storing the electrical signals obtained during the scan by each of the facets. In an embodiment of this form of the invention, the facets implement focusing at different depth ranges in the body, and the stored signals are range-gated out of storage for B-scan display of echo amplitude as a function of range.

Further features and advantages of the invention will become more readily apparent from the following detailed description when taken in conjunction with the accompanying drawings.

DETAILED DESCRIPTION

Figure 1:
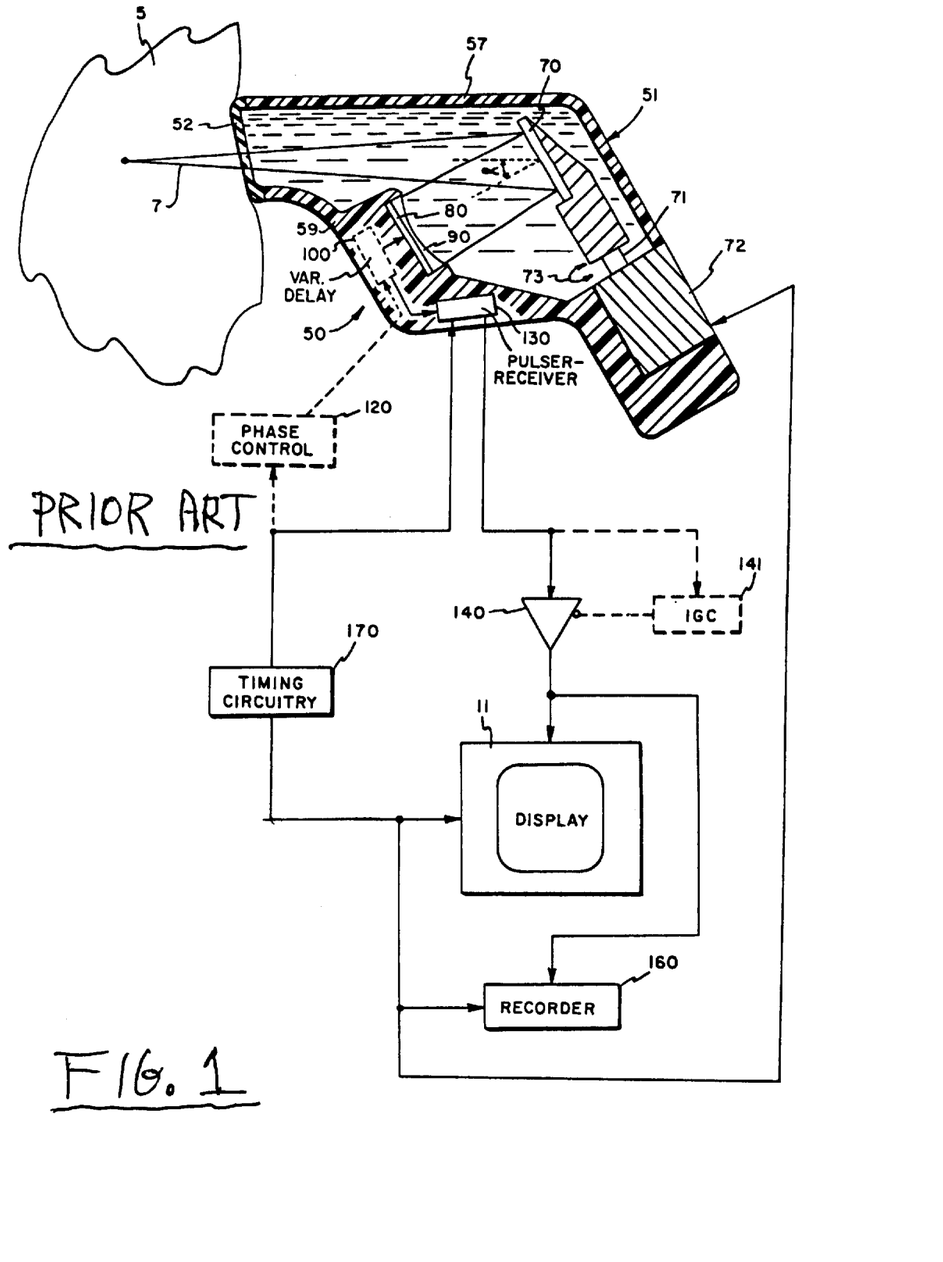
FIG. 1 is a diagram, partially in cross-section and partially in block form, of an apparatus and technique of the prior art.

Referring to FIG. 1, there is shown an illustration of a prior art ultrasonic scanning and imaging apparatus as set forth in the above referenced U.S. Pat. No. 4,325,381. A console 10 is provided with a display 11 which may typically be a conventional monitor. A suitable recorder 160 is also provided. In present day parlance, some of he console functions described in the '381 Patent can be implemented with a personal computer, which typically include the power supplies, timing (170), and processing functions analagous to those described in the Patent. A portable scanning mode or probe 50 is coupled to the console. The probe has a generally cylindrical handle and a scanning window 52 near one end. During operation of the apparatus, the probe 50 is hand-held to position the scanning window over a part of the body 5 to be imaged. Imaging of other portions of the body is readily attained by moving the probe to the desired position and orientation. The position and orientation of the scanning window determines the cross-section imaged by the equipment.

In the cross-sectional view of the probe 50 of FIG. 1, an enclosure 51, formed of a plastic, has the scanning window 52 at the front end thereof. The enclosure 51 is filled with a suitable fluid 57, for example, water. Presently, mineral oil can also be used. The scanning window 52 is described as being formed, for example, of polystyrene or nylon. A reflective scanning mirror 70 is positioned at the approximate rear of the enclosure 51 and faces the window 52. The scanner 70 is mounted on a shaft 71 which passes through a suitable seal and is connected to an electric motor 72 which is mounted in a recess in enclosure 51 and is driven to provide the motion of scanner 70, depicted in the Patent by curved two-headed arrow 73 as an oscillatory motion. An ultrasonic transducer 80, which may have an associated focusing lens 90, is mounted in a compartment 59 of enclosure 51. The transducer is mounted relatively frontwardly of reflective scanner 70 in the module 50 with the ultrasound-emitting face of the transducer generally facing rearwardly in the module 50 and being directed toward the reflective scanner 70. The transducer 80 is positioned such that the ultrasound beam which it emits is reflected by the scanner 70 to double back past transducer 80 before passing through the window 52. The scanner is described as preferably having a reflective surface formed of a material which results in a relatively small critical angle so that the beam impinging almost directly on the reflector surface will not pass through the reflector. The described arrangement is stated to make efficient use of the volume of fluid 57 in the module 50 since the beam 7 is effectively "doubling back" past the transducer and experiencing a relatively large travel distance through a relatively small volume of water. A pulser/receiver circuit 130 alternatively provides energizing pulses to and receives echo signals from the transducer 80. The term pulser/receiver is stated to include any combined or separate circuits for producing the energizing signals for the transducer and receiving echo signals therefrom. If dynamic focusing were employed, the transducer 80 may be segmented and the pulser/receiver circuitry 130 may be coupled to the segments of transducer 80 via variable delay circuitry 100, shown in dashed line. The pulser/receiver circuitry 130 and the variable delay circuitry 100 (if present) are stated to typically, although not necessarily, be located in the scanning module 50, for example, within the compartment 59. The receiver portion of circuit 130 is coupled through an amplifier 140 to display 11 and to recorder 160. Also, gain control circuitry including an interactive gain compensation ("IGC") capability, as represented by the block 141 (shown in dashed line), can be employed. This circuitry compensates the amplitude of later arriving signals for attention experienced during passage through body tissue and losses due to prior reflections. Accordingly, if an IGC capability is employed, the amplifier 140 may be used as a gain control amplifier under control of an IGC signal from circuit 141. Timing circuitry 170 generates timing signals which synchronize operation of the system, the timing signals being coupled to pulser/receiver 130. As described, if dynamic focusing is employed, the timing signals can also be coupled to phase control circuitry 120 which produces signals that control the variation of the delays in variable delay circuit 100. Also, a lens 90, which has a relatively flat surface bonded to the transducer and a curved concave surface which provides focusing of the beam emanating from the transducer, can be employed in the scanning module 50. It is noted in the Patent, however, that alternative means of focusing can be employed, such as electronic focusing using a segmented transducer, or providing curvature in the transducer or reflector surface.

Operation of the '381 Patent system is described as follows: Upon command from the timing circuits the pulser in circuitry 130 generates pulses which excite the transducer 80, the segments of transducer 80 being excited via variable delay circuitry 100, under control of phase control circuitry, when dynamic focusing is employed. (As is known in the art, the depth of focus can be varied electronically in a dynamically focused system by imparting predetermined delays or phase changes to different segments of the transducer 80. In such case the ultrasound pulse is typically launched with the variable delay circuitry set so that the transmitted beam is focused at a point which is between the center of the field and the deepest point within the body at which an image is being sought.) The beam of ultrasound resulting from pulsing the transducer is reflected by reflector 70 through the window 52 and into the body 5. The timing circuitry now causes the pulser/receiver 130 to switch into a "receive" or "listen" mode. (If dynamic focusing is employed, a cycle of the phase control circuitry 120 is activated.) Now, as the ultrasound echoes are received from the body via window 52 and reflected off scanner 70 toward transducer 80, the transducer serves to convert the received ultrasound energy into electrical signals. (Again, for a dynamic focusing implementation, the transducer segments serve to convert the received ultrasonic energy into electrical signals which are combined in proper phase relationship for focusing on particular reflection origination points in the range of depths being investigated.) For a two-dimensional "B-scan" display, a sweep over the range of depth corresponds to a horizontal scanline of the display, so the timing signals from circuitry 170 synchronize the display such that the active portion of one scanline of the display corresponds to the time of arrival of echoes from a given range within the body 5, typically from the patient's skin up to a fixed preselected depth in the body. The second dimension of the desired cross-sectional image is attained by the slower mechanical scan of reflective scanner 70 which is synchronized with the vertical scan of the display and recorder. The received signals are coupled through amplifier 140 to display 11 wherein the received signals modulate the brightness of the scanning raster to obtain the desired cross-sectional image, with each scanline of the television-type display representing a depth echo profile of the body for a particular angular orientation of the scanner 70. As also noted, the transducer 80 may have a generally elliptical shape and its preferably elongated along the direction of the scan. The reflector 70 and window 52 can also be elongated along the direction of the scan.

As first noted in the Background section hereof, the window in the '381 Patent is in the form of an acoustic lens for converging the scan of the ultrasound beam incident thereon from within the enclosure. The acoustic lens thereby serves to reduce geometric distortion of the scan of the ultrasound beam.

As first noted in the Summary section hereof, in the geometry described in the '381 Patent, it was not possible to have the center of the scan to be at the focal point of the window lens (lens membrane). A form of the present invention overcomes this deficiency.

It has been found that it is generally preferable to vary the focus of the scanner rather than use dynamic focus. Variable focus maximizes the intensity and resolution at all ranges. The focus cannot be varied dynamically in transmit. In my U.S. Pat. No. 4,257,271, selectable focus was achieved using a tapped delay line and a transducer with multiple electrodes. In accordance with a further form of the invention, a variable focus technique is implemented mechanically rather than electronically. This provides a continuous variation in focus without requiring multiple electrodes on the transducer.

There are certain requirements for a scanner that has a Cartesian scan and that keeps the aperture (and consequently, the azimuth resolution) constant at all ranges. The path length from the transducer to the skin should be an integral multiple of the round trip distance the sound travels between transmit pulses. There are multiple reflections from the membrane and transducer since they are parallel to each other. This distance requirement places these multiple reflections at the membrane surfaces in the image where it cannot obscure useful information at greater depths. In previous designs, this distance was chosen to be equal to the depth of the longest range displayed by the system. Because of this, the scanning mirror had to be at a much shorter distance than this from the membrane. The focal length of the lens membrane cannot be made short enough at a reasonable scanning width to have its focal point at the center of deflection of the beam.

In a form of the present invention, a distance of twice the depth of penetration is chosen between the transducer and the membrane. The scanning mirror is placed at the depth of penetration before the membrane. The focal length of the lens membrane can now be made equal to the depth of penetration, which is also equal to the distance from the mirror to the membrane.

Figure 2:
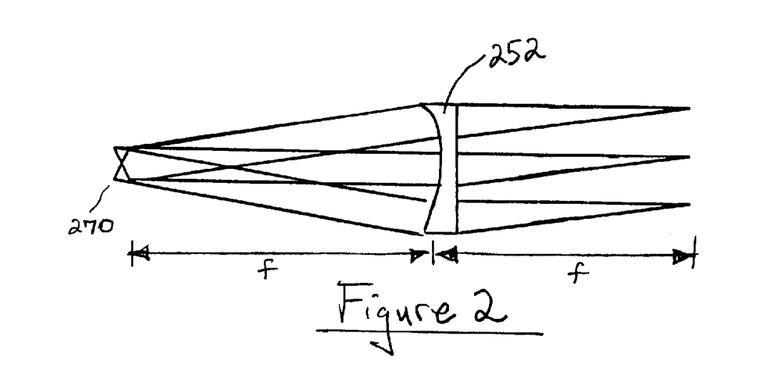
FIG. 2 illustrates a scan useful in understanding a form of the invention.

In the diagram of FIG. 2, the scanning mirror is represented at 270, and the window lens (or lens membrane) at 252. When the beam is collimated entering the membrane, it is focused at the maximum range in the tissue. Since the center of deflection is at the focal length of the lens membrane, the scan will be parallel. The focus of the beam can be varied from collimated to focused at the membrane surface. One way of doing this is to use a scanning mirror that is itself a thin elastic membrane with air behind it. Rubber or nylon are examples of suitable materials for this mirror membrane. The curvature of the membrane can be varied from flat to concave by changing the pressure in the scanning head.

Figure 3:
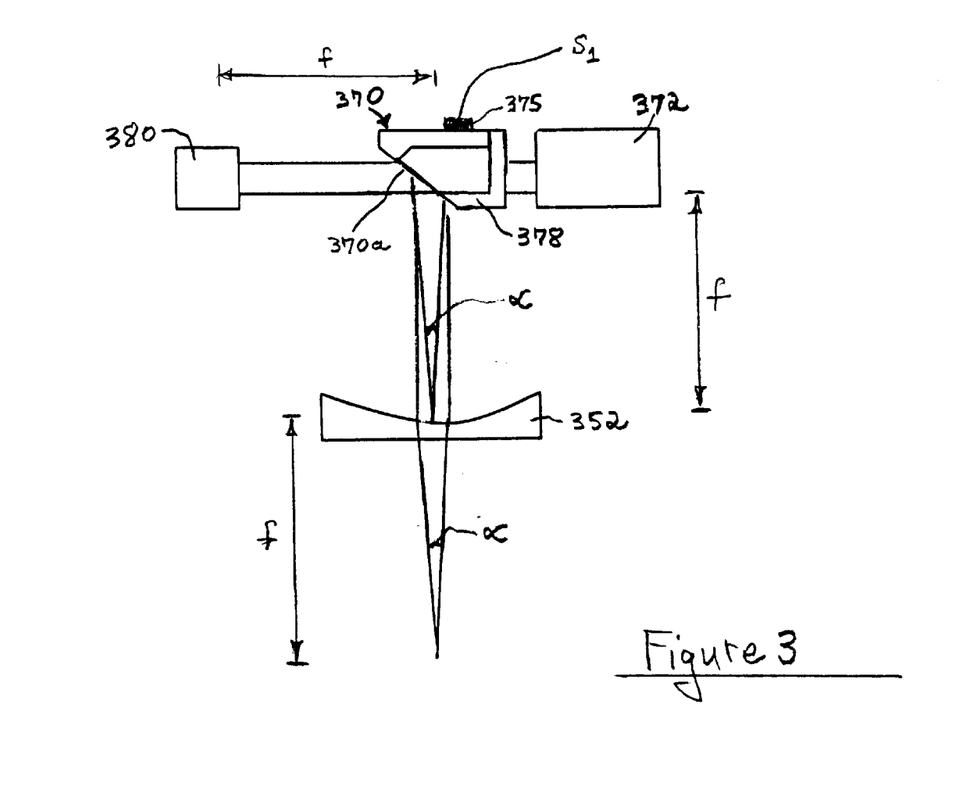
FIG. 3 is a diagram, partially in cross-section and partially in block form, of an apparatus in accordance with an embodiment of the invention and which can be utilized in practicing a form of the method of the invention.

An example of the scanning structure is shown in FIG. 3, wherein the transducer (which can have an associated focusing lens or a focusing curvature, as described hereinabove) is labelled 380, the variable focusing scanner is represented at 370 and is driven by motor 372, and the window lens (or lens membrane) is represented at 352. In this case, the beam is scanned for a complete revolution and the active part of the scan is stored for the interval used. Note that the angle α stays constant at all ranges. If 12 revolutions per second is used, the active scan would be about ⅕ of a revolution. By making the air-containing scanner housing slightly flexible, the pressure can be changed by squeezing the chamber slightly to shorten the focal distance of the scanner by changing the shape of reflective membrane 370a. This can be implemented, for example, with a transducer 375 under control of signal $S_1$ from a processor.

Figure 4:
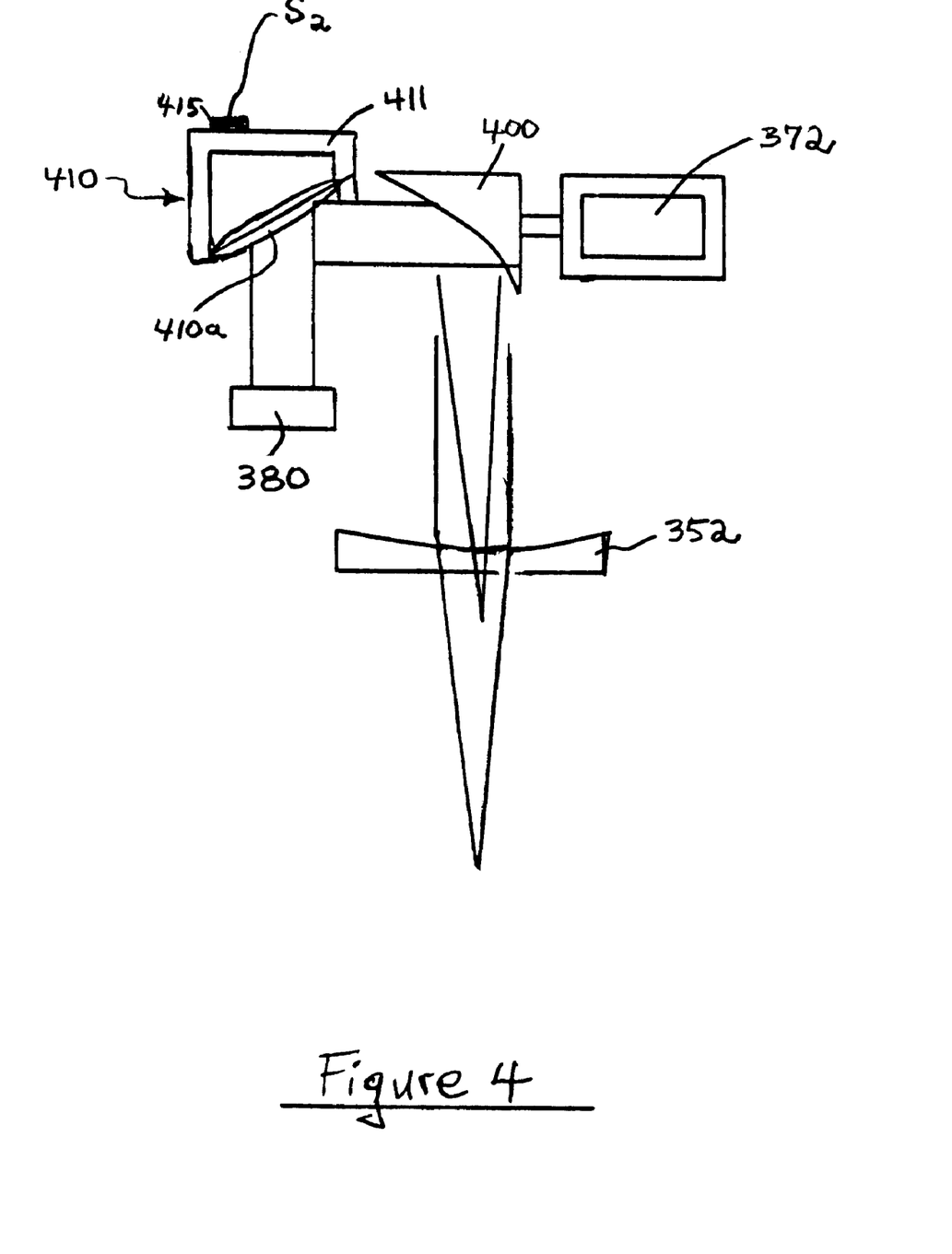
FIG. 4 is a diagram, partially in cross-section and partially in block form, of an apparatus in accordance with another embodiment of the invention and which can be utilized in practicing another form of the method of the invention.

The turbulence created by the rotating mirror may distort the membrane 370a slightly. An alternative is to use a rigid concave scanning mirror as shown at 400 in FIG. 4. In this embodiment, a separate non-rotating variable focus reflector 410 is employed, having reflective membrane 410a, the shape of which is controlled by transducer 415 on air-containing flexible housing/enclosure 411. The signal $S_2$ controls the focusing of variable focus reflector 410. In this embodiment, the scanning reflector preferably has a parabolic surface with its focal point at the far range in the body tissue. The lens membrane 352 will then refocus this beam in the midfield. The variable mirror assembly 410 is used to adjust this focal point from the far field to the near field.

Figure 5:
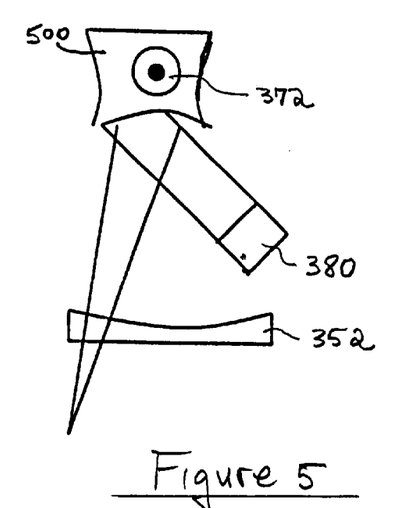
FIG. 5 is a diagram, partially in cross-section and partially in block form, of an apparatus in accordance with a further embodiment of the invention and which can be utilized in practicing a further form of the method of the invention.
Figure 6:
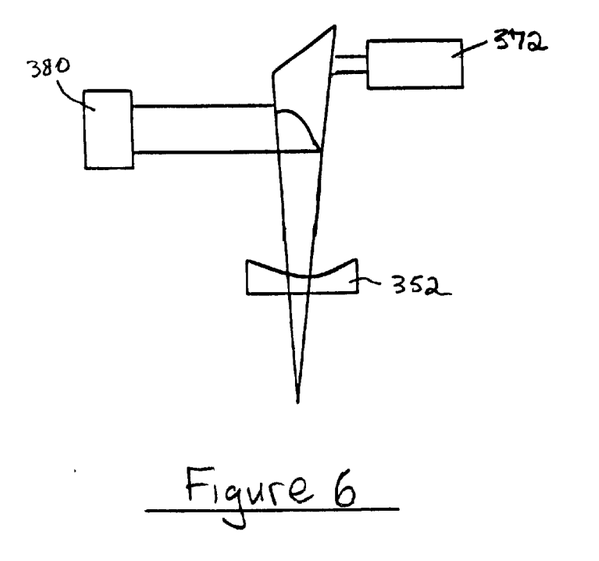
FIG. 6 is a diagram, partially in cross-section and partially in block form, of an apparatus in accordance with a still further embodiment of the invention and which can be utilized in practicing a still further form of the method of the invention.

A further embodiment uses a scanning mirror with a plurality, such as four or more, reflective facets. Each facet can be provided with a different focal length. These can be, for example, a 45° polygon or a multifaceted cylinder. The timing is synchronized to select which facet to use for scanning during a particular time frame. FIG. 5 shows the 45° configuration with multifaceted reflective scanner 500. In FIG. 6, the facets of reflective scanner 600 reflect a beam substantially offset from the axis of rotation of the scanner. This permits a shorter distance from transducer to scanner, since the effective focal length to the lens membrane is measured from the rotation axis.

Figure 7A:
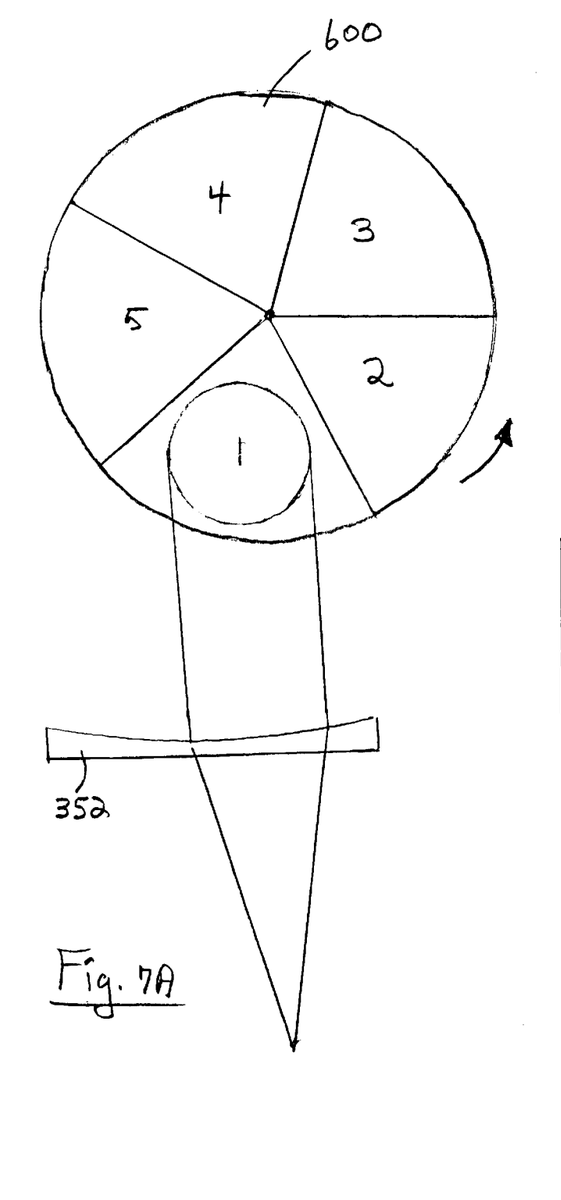
FIGS. 7A and 7B are diagrams useful in understanding operation of embodiments of the invention utilizing several facets of respectively different focal lengths.
Figure 7B:
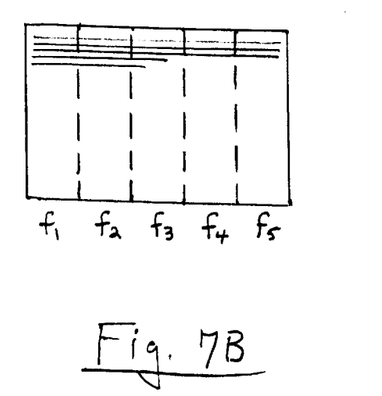

FIGS. 7A and 7B illustrates operation of a feature of the embodiments of FIGS. 5 and 6. In the present example, the scanning reflector 600 has five facets, with five different characteristic focal lengths labeled 1, 2, 3, 4, and 5. In the illustration, at the particular time shown, the ultrasound beam is being reflected from facet 1 which, in this example, has the shortest focal length. The beam reflected from this facet is further focused by the window lens 352, as shown. In this example, two memories can be used, one of them loading while the other is being read out at, for example, 60 frames per second. When facet 1 is scanning, the first 10 microseconds of data after the transmit pulse is loaded into memory. In this example, the facet 2 has the second shortest focal length. The data for the next 10 microsecond interval is loaded during the second sector scan, and so on. Thus, as depicted in FIG. 7B, the results of the data taken during scanning by facet 1 are in the leftmost sector (dashed line column), the data resulting from the scan of the facet 2 is in the second column, and so on. As actually displayed, however, after range-gated read-in, each display scan line comprises 10 microseconds of data from facet 1, the next 10 microseconds of data from facet 2, and so on, so that the overall depth dimension on the display encompasses a continuum of five (for this example) well focused regions.

What is claimed is:

1. For use in an apparatus for ultrasonically imaging sections of a body by transmitting ultrasonic energy into the body and determining the characteristics of the ultrasonic energy reflected therefrom, said apparatus including timing means for generating timing signals; energizing/receiving means operative in response to timing signals; and display/record means synchronized with said timing signals for displaying and/or recording image-representative signals from the energizing/receiving means; said apparatus having a scanning module that includes: a fluid-containing enclosure having an ultrasonically-transmissive window which can be placed in contact with the body; transducer means, in said enclosure, coupled to said energizing/receiving means, for converting electrical energy to a beam of ultrasonic energy and for converting reflected ultrasonic energy to electrical signals; means for focusing the ultrasound beam emanating from said transducer means; reflective scanning means rotatably mounted in said enclosure in the path of said ultrasound beam for effecting scanning of said beam across said body via said window; said window comprising an acoustic lens for converging the scan of the ultrasound beam incident thereon from within said enclosure; a method comprising the steps of:

selecting a desired maximum depth of penetration of said ultrasound beam into the body;

providing distances between said transducer means and said reflective scanning means and between said reflective scanning means and said acoustic lens window that are each substantially equal to said selected maximum depth of penetration.

2. The method as defined by claim 1, further comprising the step of varying the focusing of the ultrasound beam impinging on the acoustic lens window between a collimated beam and a focused beam.

3. The method as defined by claim 2, wherein said step of varying the focusing of the ultrasound beam comprises varying the shape of said reflective scanning means.

4. The method as defined by claim 2, wherein said step of varying the focusing of the ultrasound beam comprises providing a variable focusing ultrasound reflector in the path of said ultrasound beam.

5. The method as defined by claim 4, wherein said step of providing a variable focusing ultrasound reflector includes providing an ultrasound reflector having a controllable shape.

6. The method as defined by claim 5, wherein said step of providing an ultrasound reflector having a controllable shape comprises providing said ultrasound reflector as part of a cavity enclosure whose shape is controllable by controlling the pressure in said cavity.

7. For use in an apparatus for ultrasonically imaging sections of a body by transmitting ultrasonic energy into the body and determining the characteristics of the ultrasonic energy reflected therefrom, said apparatus including timing means for generating timing signals; energizing/receiving means operative in response to timing signals; and display/record means synchronized with said timing signals for displaying and/or recording image-representative signals from the energizing/receiving means; said apparatus having a scanning module that includes: a fluid-containing enclosure having an ultrasonically-transmissive window which can be placed in contact with the body; transducer means, in said enclosure, coupled to said energizing/receiving means, for converting electrical energy to a beam of ultrasonic energy and for converting reflected ultrasonic energy to electrical signals; means for focusing the ultrasound beam emanating from said transducer means; reflective scanning means rotatably mounted in said enclosure in the path of said ultrasound beam for effecting scanning of said beam across said body via said window; said window comprising an acoustic lens for converging the scan of the ultrasound beam incident thereon from within said enclosure; a method comprising the steps of:

providing, on said rotatable reflective scanning means, a plurality of ultrasound reflecting facets having different focusing characteristics; and storing the electrical signals obtained during the scan by each of said facets.

8. The method as defined by claim 6, wherein said step of providing, on said rotatable reflective scanning means, a plurality of facets, comprises providing several such facets having respectively different focusing characteristics.

9. The method as defined by claim 6, wherein said facets implement focusing at different depth ranges in the body, and wherein said stored signals are range-gated out of storage for display.

10. The method as defined by claim 8, wherein said facets implement focusing at different depth ranges in the body, and wherein said stored signals are range-gated out of storage for display.

11. The method as defined by claim 9, wherein said signals are range-gated out as a continuous B-scan display of echo amplitude as a function of range.

12. The method as defined by claim 10, wherein said signals are range-gated out as a continuous B-scan display of echo amplitude as a function of range.

13. The method as defined by claim 7, wherein said step of providing, on said rotatable reflective scanning means, a plurality of ultrasound reflecting facets, includes offsetting the axis of rotation with respect to the axis of said ultrasound beam.

14. The method as defined by claim 9, wherein said step of providing, on said rotatable reflective scanning means, a plurality of ultrasound reflecting facets, includes offsetting the axis of rotation with respect to the axis of said ultrasound beam.

* * * * *